(12) United States Patent
Acharya et al.

(10) Patent No.: US 7,477,928 B2
(45) Date of Patent: Jan. 13, 2009

(54) METHOD AND SYSTEM FOR ASSOCIATING AN EKG WAVEFORM WITH A CT IMAGE

(75) Inventors: Kishore C. Acharya, Brookfield, WI (US); Darin R. Okerlund, Muskego, WI (US); Steven J. Woloschek, Franklin, WI (US); Mark E. Woodford, Waukesha, WI (US)

(73) Assignee: GE Medical Systems Global Technology Company, LLC, Weukesha, WI (US)

( * ) Notice: Subject to any disclaimer, the term of this patent is extended or adjusted under 35 U.S.C. 154(b) by 1303 days.

(21) Appl. No.: 10/063,840

(22) Filed: May 17, 2002

(65) Prior Publication Data

US 2003/0216641 A1 Nov. 20, 2003

(51) Int. Cl.
*A61B 5/05* (2006.01)
(52) U.S. Cl. .............. 600/428; 600/413; 600/425; 378/4; 378/5; 378/8; 378/14; 378/21
(58) Field of Classification Search ........... 378/8, 378/4, 14, 5, 21, 62; 600/425, 407, 410, 600/417, 428, 413
See application file for complete search history.

(56) References Cited

U.S. PATENT DOCUMENTS

| 4,182,311 | A | * | 1/1980 | Seppi et al. ............ 600/428 |
| 4,641,328 | A | * | 2/1987 | Fujise .................. 378/8 |
| 4,868,747 | A |   | 9/1989 | Mori et al. ........... 364/413.18 |
| 5,383,231 | A | * | 1/1995 | Yamagishi ............. 378/15 |
| 6,154,516 | A | * | 11/2000 | Heuscher et al. ...... 378/15 |
| 6,266,553 | B1 | * | 7/2001 | Fluhrer et al. ........ 600/428 |
| 6,285,898 | B1 | * | 9/2001 | Ben-Haim ............. 600/374 |
| 6,307,910 | B1 | * | 10/2001 | Acharya et al. ....... 378/4 |
| 6,381,487 | B1 | * | 4/2002 | Flohr et al. .......... 600/425 |
| 6,438,196 | B1 | * | 8/2002 | Cesmeli ............... 378/8 |
| 2002/0118790 | A1 | * | 8/2002 | Pan et al. ............ 378/8 |
| 2002/0126794 | A1 | * | 9/2002 | Rasche et al. ........ 378/8 |

FOREIGN PATENT DOCUMENTS

EP 1 072 224 A2 1/2001

\* cited by examiner

*Primary Examiner*—Brian L. Casler
*Assistant Examiner*—Baisakhi Roy
(74) *Attorney, Agent, or Firm*—Cantor Colburn LLP

(57) ABSTRACT

A method for associating EKG waveform data with computed tomography image data using a data synchronization scheme including generating the EKG waveform data using an electrocardiogram device, operating a computed tomography imaging system so as to create the computed tomography image data, communicating an exposure marker-in signal to the electrocardiogram device such that the exposure marker-in signal is associated with the EKG waveform data and processing the computed tomography image data, the EKG waveform data and the exposure marker-in signal, so as to correlate the EKG waveform data with the computed tomography image data. Also claimed is a medium encoded with a machine-readable computer program code for associating EKG waveform data with image data generated by an imaging system using a data synchronization scheme, the medium including instructions for causing controller to implement the aforementioned method.

30 Claims, 5 Drawing Sheets

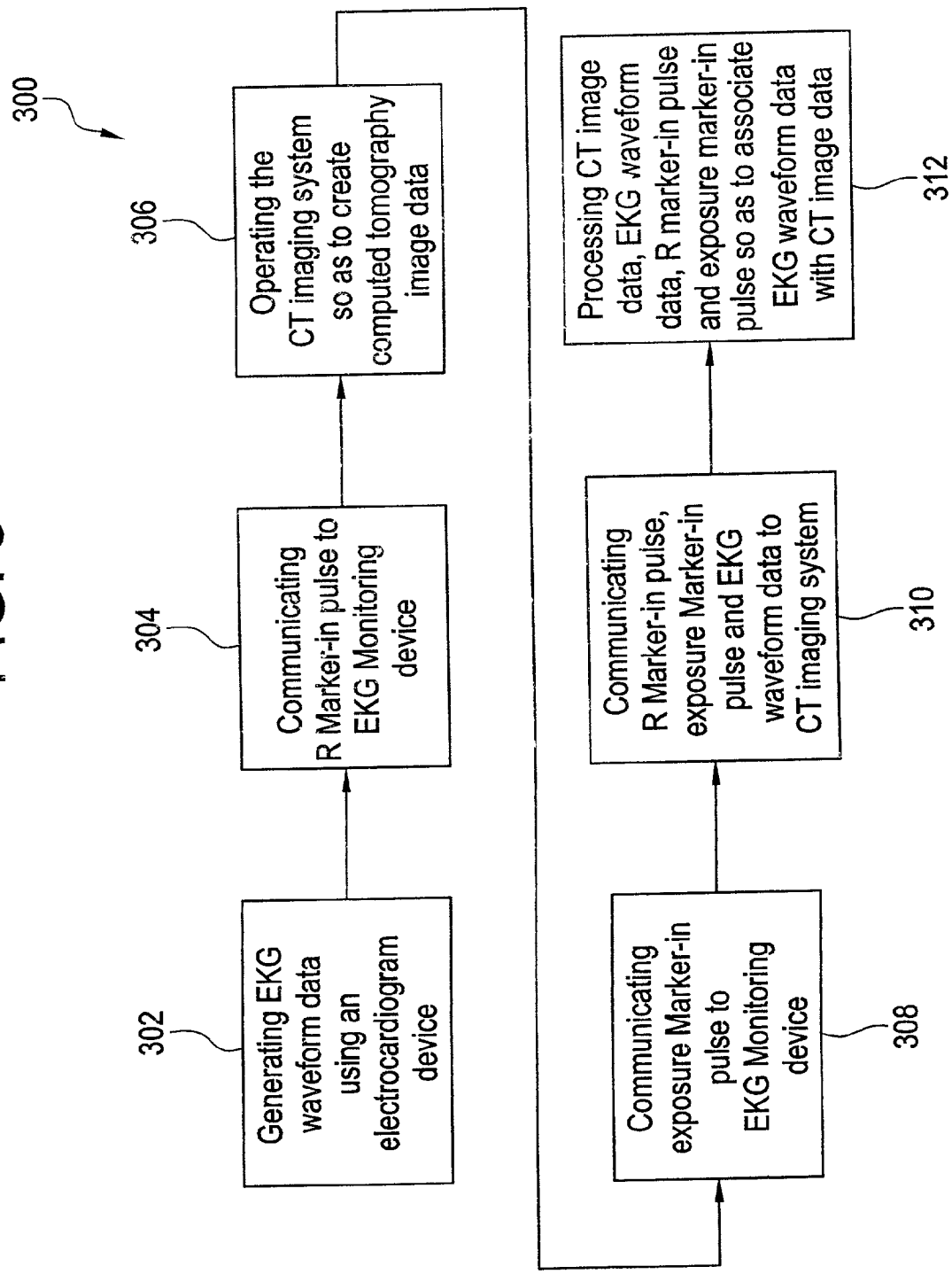

METHOD AND SYSTEM FOR ASSOCIATING AN EKG WAVEFORM WITH A CT IMAGE

BACKGROUND OF INVENTION

This invention relates generally to a method and system for synchronizing multiple data signals and more particularly to a method and system for synchronizing an EKG waveform generated via an electrocardiogram (EKG) with an x-ray image generated via a computed tomography (CT) imaging system.

In many cardiac applications, it is desirable to have the ability to display a CT image of a patients' heart along with a simultaneously generated patient EKG waveform. This would allow a physician or technician to visually observe the physical condition of the patients' heart while simultaneously observing the cardiac electrical function of a patient. However, if the heart is moving or beating (cardiac motion) during the scanning process, the CT projection data may include motion artifacts and other noises making accurate reconstruction of the CT image more difficult, or in some cases impossible.

One technique currently available to reduce the effect of cardiac motion is to synchronize the CT imaging system with the patient heart cycle so that the CT scans only occur between heart beats. In order to accomplish this task, current cardiac scanning techniques synchronize a patient CT scan with the electrical heart cycle of the patient via an EKG monitoring device communicated with a CT imaging system. Referring to FIG. 1, an example of a patient EKG waveform 100 is shown and includes an R-Peak 102 and an exposure indicator 104, wherein exposure indicator 104 identifies the period in EKG waveform 100 where the CT scan and thus patient exposure occurs. As can be seen, exposure indicator 104 is disposed between heartbeats indicating that the CT scan occurred while the patients' heart was resting.

One problem with this technique is that, although most EKG monitoring devices provide a means to read EKG waveform data as it is being collected, most CT imaging systems do not. As a result, a delay in time occurs between the collection of the EKG data and the collection of the CT projection data making accurate correlation between the EKG data and the CT projection data extremely difficult or impossible. Therefore, there is a need for a method that facilitates the correlation of EKG data and CT projection data, wherein the method utilizes existing CT imaging systems and EKG monitoring devices and wherein the method does not significantly increase the data collection time.

SUMMARY OF INVENTION

The above discussed and other drawbacks and deficiencies are overcome or alleviated by a method for associating EKG waveform data with computed tomography image data using a data synchronization scheme comprising: generating the EKG waveform data using an electrocardiogram device; operating a computed tomography imaging system so as to create the computed tomography image data; communicating an exposure marker-in signal to the electrocardiogram device such that the exposure marker-in signal is associated with the EKG waveform data; and processing the computed tomography image data, the EKG waveform data and the exposure marker-in signal, so as to correlate the EKG waveform data with the computed tomography image data.

A medium encoded with a machine-readable computer program code for associating EKG waveform data with computed tomography image data using a data synchronization scheme, the medium including instructions for causing a controller to implement a method comprising: generating the EKG waveform data using an electrocardiogram device; operating a computed tomography imaging system so as to create the computed tomography image data; communicating an exposure marker-in signal to the electrocardiogram device such that the exposure marker-in signal is associated with the EKG waveform data; and processing the computed tomography image data, the EKG waveform data and the exposure marker-in signal, so as to correlate the EKG waveform data with the computer tomography image data.

A method for associating EKG waveform data with image data generated by an imaging system using a data synchronization scheme comprising: obtaining the imaging system, an electrocardiogram device and an object to be examined; associating the object with the imaging system and the electrocardiogram device; and processing the image data and the EKG waveform data using the data synchronization scheme wherein the data synchronization scheme, generates the EKG waveform data using an electrocardiogram device; operates the imaging system so as to create the image data; communicates an exposure marker-in signal to the electrocardiogram device such that the exposure marker-in signal is associated with the EKG waveform data; and processes the image data, the EKG waveform data and the exposure marker-in signal, so as to correlate the EKG waveform data with the image data.

A system for associating EKG waveform data with computed tomography image data using a data synchronization scheme comprising: a gantry having an x-ray source and a radiation detector array, wherein the gantry defines an object cavity and wherein the x-ray source and the radiation detector array are rotatingly associated with the gantry so as to be separated by the object cavity; an object support structure movingly associated with the gantry so as to allow communication with the object cavity; and a processing device having the data synchronization scheme, wherein the data synchronization scheme, generates the EKG waveform data using an electrocardiogram device; operates a computed tomography imaging system so as to create the computed tomography image data; communicates an exposure marker-in signal to the electrocardiogram device such that the exposure marker-in signal is associated with the EKG waveform data; and processes the computed tomography image data, the EKG waveform data and the exposure marker-in signal, so as to correlate the EKG waveform data with the computer tomography image data.

A system for associating EKG waveform data with image data using a data synchronization scheme comprising: an imaging system; an object disposed so as to be communicated with the imaging system, wherein the imaging system generates image data responsive to the object; and a processing device having the data synchronization scheme, wherein the data synchronization scheme, generates the EKG waveform data using an electrocardiogram device; operates the imaging system so as to create the image data; communicates an exposure marker-in signal to the electrocardiogram device such that the exposure marker-in signal is associated with the EKG waveform data; and processes the image data, the EKG waveform data and the exposure marker-in signal, so as to correlate the EKG waveform data with the image data.

The above discussed and other features and advantages of the present invention will be appreciated and understood by those skilled in the art from the following detailed description and drawings.

BRIEF DESCRIPTION OF DRAWINGS

Referring to the exemplary drawings wherein like elements are numbered alike in the several Figures:

FIG. 5 is a flow diagram describing a method for synchronizing an EKG waveform with a CT image, in accordance with an exemplary embodiment.

DETAILED DESCRIPTION

In accordance with an exemplary embodiment, while a method and system for synchronizing EKG waveform data with an x-ray image is described and discussed hereinbelow with reference to a computed tomography (CT) imaging system, it should be understood that the method and system of the invention may be applied to other imaging systems, such as Magnetic Resonance Imaging (MRI) and/or Positron Emission Tomography (PET).

Figure 1:
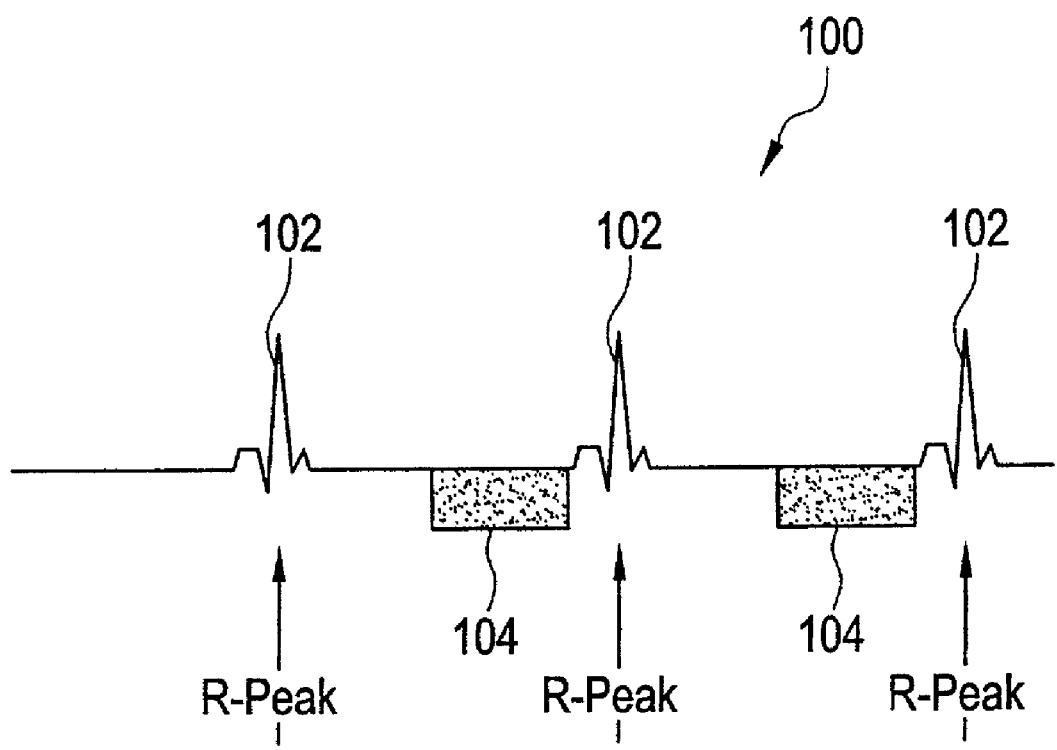
FIG. 1 is an example of an EKG waveform illustrating the timing between a CT exposure and a patient cardiac rhythm.
Figure 2:
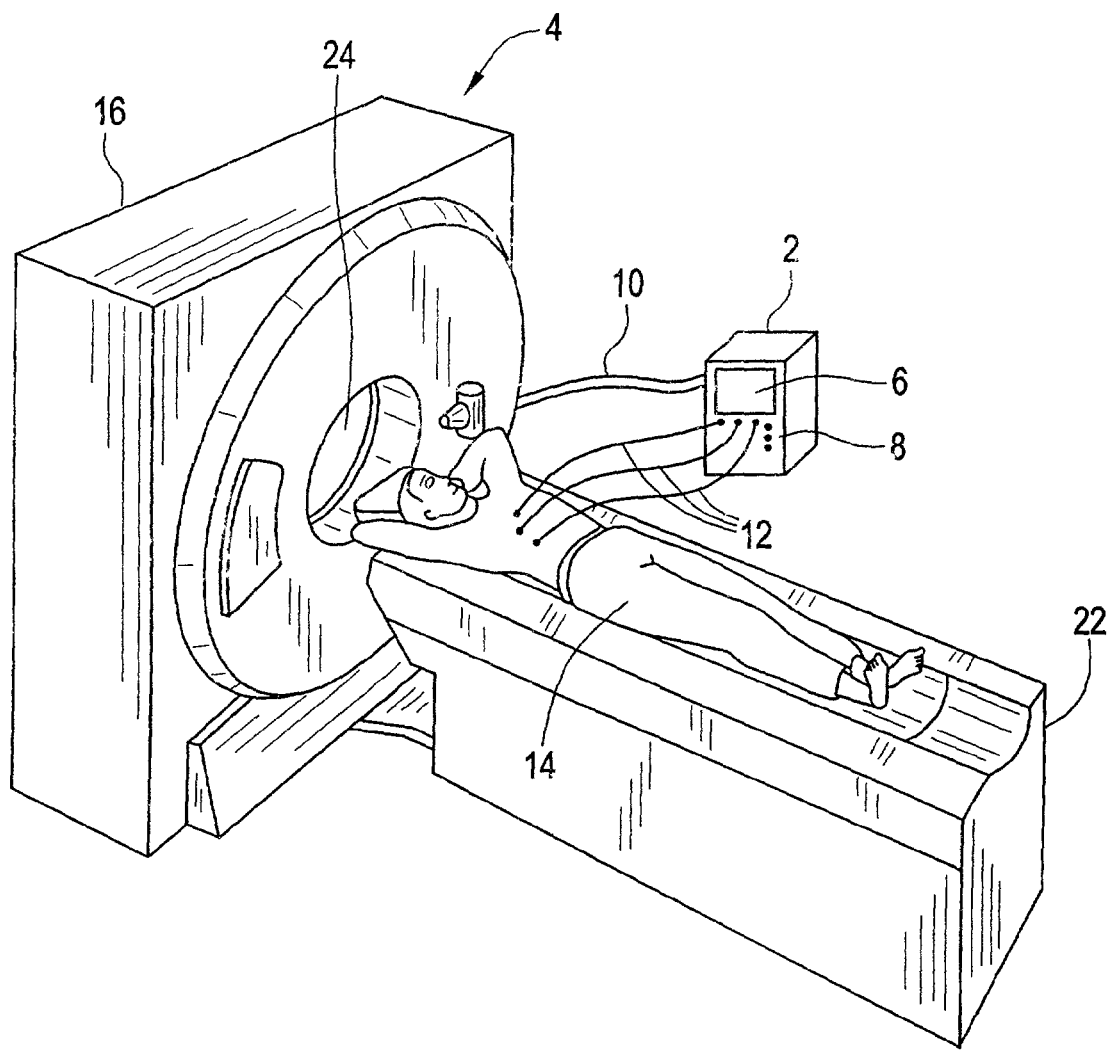
FIG. 2 is a perspective view of an EKG monitoring device communicated with a CT imaging system.
Figure 3:
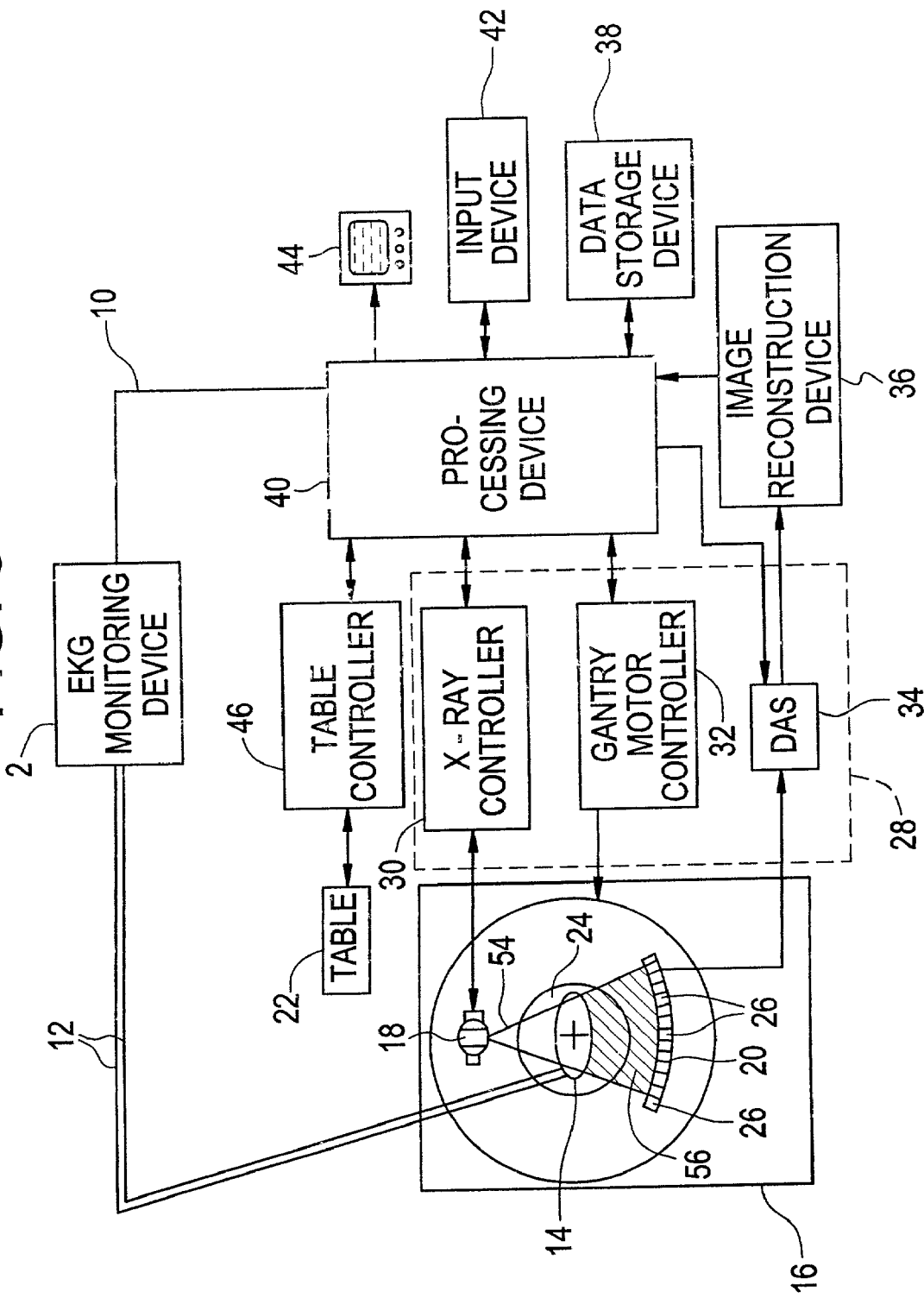
FIG. 3 is a block schematic diagram of a CT imaging system communicated with an EKG monitoring device.

Referring to FIG. 2 and FIG. 3, an EKG monitoring device 2 and a CT imaging system 4 is shown, wherein EKG monitoring device 2 is communicated with CT imaging system 4. EKG monitoring device 2 includes an EKG output 6, an EKG sync marker input 8, an EKG data transfer device 10 and a plurality of EKG input leads 12, wherein EKG monitoring device 2 is communicated with a patient 14 via EKG input leads 12 and wherein EKG monitoring device 2 is communicated with CT imaging system 4 via EKG data transfer device 10.

CT imaging system 4 includes a gantry 16 having an x-ray source 18, a radiation detector array 20, a patient support structure 22 and a patient cavity 24, wherein x-ray source 18 and radiation detector array 20 are opposingly disposed so as to be separated by patient cavity 24 and wherein radiation detector array 20 includes a plurality of detector elements 26. X-ray source 18 and radiation detector array 20 are rotatingly disposed relative to gantry 16 and patient support structure 22, so as to allow x-ray source 18 and radiation detector array 20 to rotate around patient support structure 22 when patient support structure 22 is disposed within patient cavity 24. X-ray source 18 and radiation detector array 20 are communicated with a control mechanism 28 associated with CT imaging system 4.

Control mechanism 28 controls the rotation and operation of x-ray source 18 and radiation detector array 20. Control mechanism 28 includes an x-ray controller 30 communicated with x-ray source 18, a gantry motor controller 32 communicated with gantry 16, and a data acquisition system (DAS) 34 communicated with radiation detector array 20, wherein x-ray controller 30 provides power and timing signals to x-ray source 18, gantry motor controller 32 controls the rotational speed and angular position of x-ray source 18 and radiation detector array 20 and DAS 34 receives electrical signal data produced by detector elements 26 and converts this data into digital signals for subsequent processing.

CT imaging system 4 also includes an image reconstruction device 36, a data storage device 38 and a processing device 40, wherein processing device 40 is communicated with EKG monitoring device 2, image reconstruction device 36, gantry motor controller 32, x-ray controller 30, data storage device 38, an input device 42 and a CT output device 44. Moreover, CT imaging system 4 also includes a table controller 46 communicated with processing device 40 and patient support structure 22, so as to control the position of patient support structure 22 relative to patient cavity 24.

Figure 4:
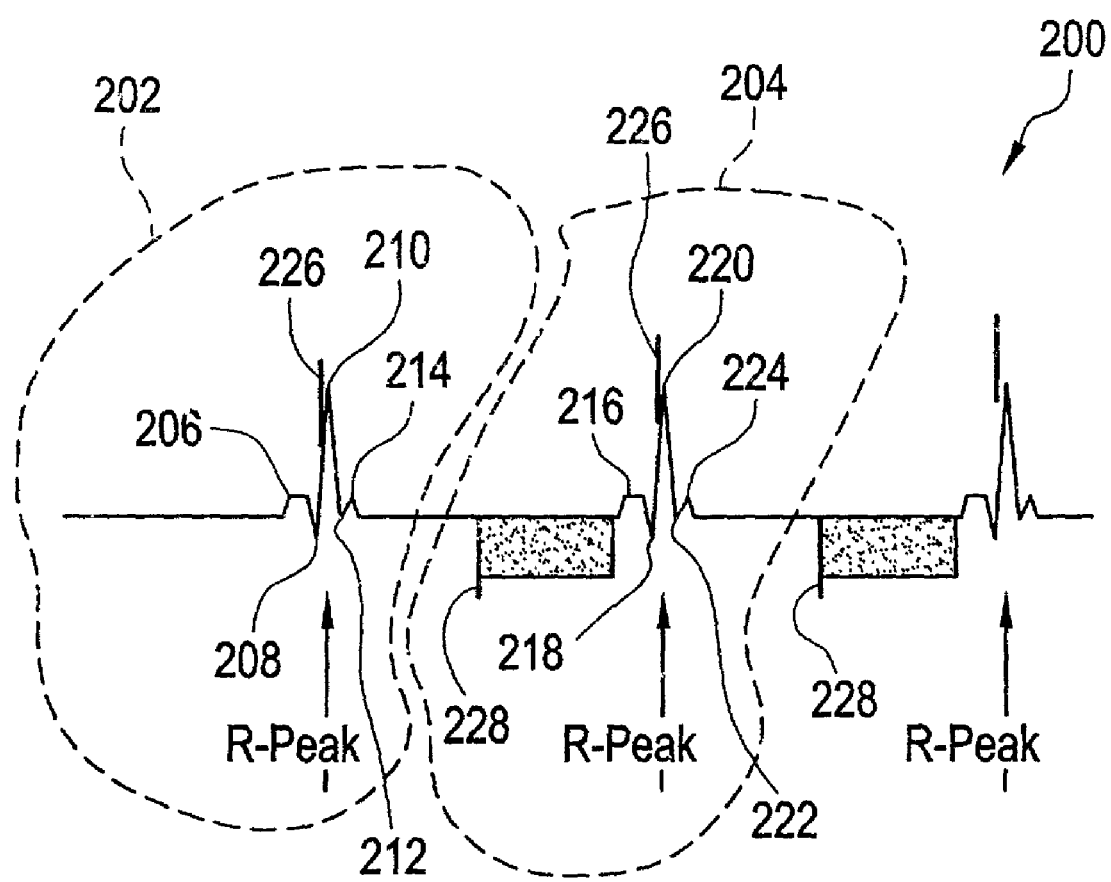
FIG. 4 is an example of an EKG waveform illustrating the synchronization timing between a CT exposure and a patient cardiac rhythm, in accordance with an exemplary embodiment.

Referring to FIG. 4, EKG waveform data 200 is shown and includes a plurality of cardiac events having a first cardiac event 202 and a second cardiac event 204. First cardiac event 202 includes a first atrial depolarization event 206, a first Q event 208, a first R-Peak event 210, a first ventricular depolarization event 212 and a first ventricular re-polarization event 214. Second cardiac event 204 includes a second atrial depolarization event 216, a second Q event 218, a second R-Peak event 220, a second ventricular depolarization event 222 and a second ventricular re-polarization event 224.

Again, referring to FIG. 2, FIG. 3 and FIG. 4, EKG monitoring device 2 and CT imaging system 4 are operated as discussed hereinbelow. Patient 14 is disposed on patient support structure 22 which is positioned so as to be within patient cavity 24. EKG input leads 12 are non-movably associated with the chest area 48 of patient 14 so as to allow EKG monitoring device 2 to receive EKG waveform data 200 from patient 14, wherein EKG waveform data 200 is responsive to the cardiac function of patient 14. As the heart of patient 14 beats, this beat is sensed by EKG input leads 12 and communicated to EKG monitoring device 2 in the form of EKG waveform data 200. EKG monitoring device 2 then examines EKG waveform data 200 so as to identify the occurrence of an R peak event 210. Upon the occurrence of an R peak event 210, EKG monitoring device 2 outputs an event signal responsive to R peak event 210, which is communicated to EKG sync marker input 8 as an R marker-in signal 226, so as to overlay EKG waveform data 200 and indicate the occurrence of an R peak event 210, wherein R marker-in signal 226, also referred to as defibrillator sync signal, is responsive to R peak event 210. Although R marker-in signal 226 is preferably a positive impulse signal, R marker-in signal 226 may be any signal suitable to the desired end purpose.

CT imaging system 4 is then preferably operated so as to create CT image data. To do this, processing device 40 instructs x-ray source 18 to emit and project a collimated x-ray beam 54 toward radiation detector array 20 so as to pass through patient 14. X-ray beam 54 passes through patient 14 so as to create an attenuated x-ray beam 56, which is received by radiation detector array 20. Detector elements 26 receive attenuated x-ray beam 56, produces electrical signal data responsive to the intensity of attenuated x-ray beam 56 and communicates this electrical signal data to DAS 34. DAS 34 then converts this electrical signal data to digital signals and communicates both the digital signals and the electrical signal data to image reconstruction device 36, which performs high-speed image reconstruction. In order to obtain a full series of scans, gantry motor controller 32 is operated via processing device 40 so as to cause x-ray source 18 and radiation detector array 20 to rotate relative to patient 14 thus generating CT image data.

As CT imaging system 4 begins to operate, CT imaging system 4 generates a CT event signal herein referred to as exposure marker-in signal 228, wherein exposure marker-in signal 228 is a negative impulse signal. Exposure marker-in signal 228 is then communicated to EKG monitoring device 2 via EKG sync marker input 8 so as to overlay EKG waveform data 200 and indicate the start of a CT scan. Although exposure marker-in signal 228 is preferably a negative impulse signal, exposure marker-in signal 228 may be any signal suitable to the desired end purpose. In addition, although exposure marker-in signal 228 is preferably generated via CT imaging system 4, exposure marker-in signal 228 may be generated via any device and/or method suitable to the desired end purpose.

The EKG waveform data 200 with the R marker-in signal 226 and the exposure marker-in signal 228 overlay are then communicated to CT imaging system 4 via EKG data transfer device 10 so as to be processed and associated with the corresponding CT imaging data. Processing device 40 does this by processing the CT imaging data and EKG waveform data 200 with the R marker-in signal 226 and the exposure marker-in signal 228 overlay so as to associate the CT image data with EKG waveform data 200. The CT image data and EKG waveform data 200 with the R marker-in signal 226 and the exposure marker-in signal 228 may then by stored via data storage device 38. Although this data association is preferably accomplished via a "time stamping" method, this data association may be accomplished via any method, process or device suitable to the desired end purpose.

Referring to FIG. 5, a method for synchronizing EKG waveform data 200 with CT image data using a data synchronization scheme 300 is shown and discussed. In accordance with an exemplary embodiment, EKG monitoring device 2 is communicated with a patient 14 via EKG input leads 12 and EKG monitoring device 2 is operated so as to generate EKG waveform data 200 responsive to the cardiac function of patient 14, as shown in step 302. EKG monitoring device 2 then examines EKG waveform data 200 so as to identify an R peak event 210. Upon the occurrence of R peak event 210, EKG monitoring device 2 outputs an event signal which is communicated to EKG monitoring device 2 via EKG sync marker input 8 as R marker-in signal 226. R marker-in signal 226 is then processed so as to be associated with R peak event 210, as shown in step 304.

CT imaging system 4 is then operated so as to create CT image data, as shown in step 306. As CT imaging system 4 begins to operate, CT imaging system 4 generates exposure marker-in signal 228, which is communicated to EKG monitoring device 2 via EKG sync marker input 8, as shown in step 308. Exposure marker-in signal 228 is then processed so as to be associated with the start of a CT scan. Once R marker-in signal 226 and exposure marker-in signal 228 have been associated with EKG waveform data 200, EKG waveform data 200, R marker-in signal 226 and exposure marker-in signal 228 are communicated to CT imaging system 4, as shown in step 310. Processing device 40 processes the CT image data, EKG waveform data 200, R marker-in signal 226 and exposure marker-in signal 228, so as to associate EKG waveform data 200 with the CT image data, as shown in step 312. This advantageously allows matching of the CT image data with the EKG waveform data 200.

In accordance with an exemplary embodiment, CT imaging system 4 determines the timing of the CT scans based off of the occurrence of an R peak event 210. This technique advantageously allows for EKG waveform synchronization with view projections for 'axial' as well as 'helical' types of cardiac scans. Moreover, EKG waveform data 200 and the CT image data are preferably correlated as follows. Once an operator initiates a CT scan, the processing device 40 starts reading EKG waveform data 200 from EKG monitoring device 2 and records this information to a file, such as data storage device 38. Once the CT scans are complete, processing device 40 examines EKG waveform data 200 for impulse functions within EKG waveform data 200 which signify a marker-in pulse, such as R marker-in signal 226 and exposure marker-in signal 228 (for example a positive impulse indicates an R peak event 210 and a negative impulse indicates the start of a CT scan). Since the rate of data acquisition of EKG waveform data 200 is known and exposure marker-in signal 228 is found, a simple calculation can be used to associate view projections of the CT image data with different parts of EKG waveform data 200.

Data synchronization scheme 300 allows for EKG waveform data to be synchronized with CT image data, thus advantageously allowing for the simultaneous examination of a patient's physical cardiac condition as well as the patient's cardiac function.

In accordance with an exemplary embodiment, data synchronization scheme 300 may be applied to image data obtained by any imaging system suitable to the desired end purpose, such as Magnetic Resonance Imaging (MRI) and/or Positron Emission Tomography (PET).

In accordance with an exemplary embodiment, processing of FIG. 5 may be implemented through processing device 40 operating in response to a computer program. In order to perform the prescribed functions and desired processing, as well as the computations therefore (e.g., the execution of fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include signal input signal filtering to enable accurate sampling and conversion or acquisitions of such signals from communications interfaces. It is also considered within the scope of the invention that the processing of FIG. 5 may be implemented by a controller located remotely from processing device 40.

As described above, the present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for associating EKG waveform data with computed tomography image data using a data synchronization scheme comprising:
   generating the EKG wave form data using an electrocardiogram device;
   operating a computed tomography imaging system so as to create the computed tomography image data;
   communicating an exposure marker-in signal to said electrocardiogram device such that said exposure marker-in signal is associated with the EKG waveform data; and
   processing the computed tomography image data, the EKG waveform data and said exposure marker-in signal, so as to correlate the EKG waveform data with the computed tomography image data.

2. The method of claim 1, wherein said generating includes operating said electrocardiogram device so as to create the EKG-waveform data, wherein the EKG waveform data is responsive to the cardiac function of a patient.

3. The method of claim 1, wherein said generating includes generating and introducing an event signal to said electrocardiogram device so as to overlay the EKG waveform data with said event signal such that said event signal is associated with the EKG waveform data.

4. The method of claim 1, wherein said communicating an exposure marker-in signal includes generating and introducing said exposure marker-in signal so as to overlay the EKG waveform data with said exposure marker-in signal.

5. The method of claim 1, wherein said electrocardiogram device includes a marker-in input and wherein said electrocardiogram device is communicated with a patient.

6. The method of claim 1, wherein said communicating includes introducing an event signal to said electrocardiogram device so as to associate said event signal with an R-peak event.

7. The method of claim 1, wherein maid communicating includes introducing said exposure marker-in signal to said electrocardiogram device so as to associate said exposure marker-in signal with the start of a computed tomography imaging system scan.

8. The method of claim 1, wherein the EKG waveform data includes an R-Peak event, an atrial depolarization event and a ventricular re-polarization event.

9. The method of claim 1, wherein said generating includes generating an event signal responsive to the EKG waveform data.

10. The method of claim 1, wherein said exposure marker-in signal is responsive to said computed tomography imaging system.

11. The method of claim 1, wherein said processing includes processing the computed tomography image data, the EKG waveform data and said exposure marker-in signal so as to associate the EKG waveform data with the computed tomography image data.

12. The method of claim 1, wherein said processing includes storing the computed tomography image data, the EKG waveform data and said exposure marker-in signal using a data storage device.

13. The method of claim 1, further comprising:
   operating the computed tomography imaging system so as to generate an exposure mark-in signal; and
   wherein said communicating an exposure marker-in signal to said electrocardiogram device comprises communicating said generated exposure marker-in signal to said electrocardiogram device.

14. The method of claim 13, wherein:
   said generated exposure marker-in signal represents a computed tomography event signal; and
   said communicated exposure marker-in signal is communicated so as to overlay the EKG waveform data and indicate the start of a CT scan.

15. A medium encoded with a machine-readable computer program code for associating EKG waveform data with computed tomography Image data using a data synchronization scheme, said medium including instructions for causing a controller to implement a method comprising:
   generating the EKG waveform data using an electrocardiogram device;
   operating a computed tomography imaging system so as to create the computed tomography image data;
   communicating an exposure marker-in signal to said electrocardiogram device such that said exposure marker-in signal ii associated with the EKG waveform data; and
   processing the computed tomography image data, the EKG waveform data and said exposure marker-in signal, so as to correlate the EKG waveform data with the computer tomography image data.

16. The medium of claim 15, wherein said generating includes operating said electrocardiogram device so as to create the EKG waveform data, wherein the EKG waveform data is responsive to the cardiac function of a patient.

17. The medium of claim 15, wherein said generating includes generating and introducing an event signal to said electrocardiogram device so as to overlay the EKG waveform data wit said event signal such that said event signal is associated with the EKG waveform data.

18. The medium of claim 15, wherein said communicating an exposure marker-in signal includes generating sad introducing said exposure marker-in signal so as to overlay the EKG waveform data with said exposure marker-in signal.

19. The medium of claim 15, wherein said communicating includes introducing an event signal to said electrocardiogram device so as to associate said event signal with an R-peak event 20. The medium of claim 15, wherein said communicating includes introducing said exposure marker-in signal to said electrocardiogram device so as to associate said exposure marker-in signal with the start of a computed tomography imaging system scan.

21. The medium of claim 15, wherein said generating includes generating an event signal responsive to the EKG waveform data.

22. The medium of claim 15, wherein said exposure marker-in signal is responsive to said computed tomography imaging system.

23. The medium of claim 15, wherein said processing includes processing the computed tomography image data, the EKG waveform data and said exposure marker-in signal so as to associate the EKG waveform data with the computed tomography image data.

24. The medium of claim 15, wherein said processing includes storing the computed tomography image data, the EKG waveform data and said exposure minter-in signal using a data storage device.

25. A method for associating EKG waveform data with image data generated by an imaging system using a data synchronization scheme comprising:

obtaining the imaging system, an electrocardiogram device and an object to be examined;

associating said object with the imaging system and said electrocardiogram device; and processing the image data and the EKG waveform data using the data synchronization scheme wherein the data synchronization scheme, generates the EKG waveform data using an electrocardiogram device;

operates the imaging system so as to create the image data;

communicates an exposure marker-in signal to said electrocardiogram device such tat said exposure marker-in signal is associated with the EKG waveform data; and processes the image data, the EKG waveform data and said exposure marker-in signal, so as to correlate the EKG waveform data with the image data.

26. A system for associating EKG waveform data with computed tomography image data using a data synchronization scheme comprising:

a gantry having an x-ray source and a radiation detector array, wherein said gantry defines an object cavity and wherein said x-ray source and said radiation detector array are rotatingly associated with said gantry so as to be separated by said object cavity;

an object support structure movingly associated with said gantry so as to allow communication with said object cavity; and a processing device having the data synchronization scheme, wherein the data synchronization scheme, generates the EKG waveform data using an electrocardiogram device;

operates a computed tomography imaging system so as to create the computed tomography image data;

communicates an exposure marker-in signal to said electrocardiogram device such that said exposure marker-in signal is associated with the EKG waveform data; and processes the computed tomography image data, the EKG waveform data and said exposure marker-in signal, so as to correlate the EKG waveform data with the computer tomography image data.

27. The system of claim 26, wherein the data synchronization scheme further, operates the computed tomography imaging system so as to generate an exposure marker-in signal; and communicates the generated exposure marker-in signal to said electrocardiogram device such that the generated exposure marker-in signal is associated wit the EKG waveform data.

28. A system for associating EKG waveform data with image data using a data synchronization scheme comprising:

an imaging system;

an object disposed so as to be communicated wit said imaging system, wherein said imaging system generates image data responsive to said object; and a processing device having the data synchronization scheme, wherein the data synchronization scheme, generates the EKG waveform data using an electrocardiogram device;

operates said imaging system so as to create the image data;

communicates an exposure marker-in signal to said electrocardiogram device such that said exposure marker-in signal is associated with the EKG waveform data; and processes the image data, the EKG waveform data and said exposure marker-in signal, so as to correlate the EKG waveform data with the image data.

29. The system of claim 28, wherein said object is a patient.

30. The system of claim 28, wherein said imaging system is a computed tomography imaging system.

* * * * *